(12) United States Patent
Siegel et al.

(10) Patent No.: US 8,583,694 B2
(45) Date of Patent: Nov. 12, 2013

(54) HEALTH-CARE RELATED DATABASE MIDDLEWARE

(75) Inventors: Jason Siegel, Calabasas, CA (US); Russell Von Blanck, Calabasas, CA (US)

(73) Assignee: Atlas Development Corporation, Calabasas, CA (US)

( * ) Notice: Subject to any disclaimer, the term of this patent is extended or adjusted under 35 U.S.C. 154(b) by 0 days.

(21) Appl. No.: 13/042,179

(22) Filed: Mar. 7, 2011

(65) Prior Publication Data

US 2011/0225176 A1  Sep. 15, 2011

Related U.S. Application Data

(63) Continuation-in-part of application No. 11/431,900, filed on May 9, 2006, now abandoned.

(60) Provisional application No. 60/679,429, filed on May 9, 2005, provisional application No. 60/718,951, filed on Sep. 19, 2005.

(51) Int. Cl.
*G06F 17/30* (2006.01)

(52) U.S. Cl.
USPC .......................................... 707/796; 707/804

(58) Field of Classification Search
USPC .................. 707/796, 793, 804, 802, 792, 759
See application file for complete search history.

(56) References Cited

U.S. PATENT DOCUMENTS

| | | | |
|---|---|---|---|
| 5,335,346 A | 8/1994 | Fabbio | |
| 5,787,437 A | 7/1998 | Potterveld et al. | |
| 6,799,184 B2 | 9/2004 | Bhatt et al. | |
| 7,133,880 B1 | 11/2006 | Nori et al. | |
| 7,194,462 B2 | 3/2007 | Riccardi et al. | |
| 7,483,924 B2 * | 1/2009 | Cohen et al. | 1/1 |
| 2003/0058277 A1* | 3/2003 | Bowman-Amuah | 345/765 |
| 2003/0074248 A1* | 4/2003 | Braud et al. | 705/9 |
| 2004/0125131 A1* | 7/2004 | Phelps | 345/738 |
| 2005/0246205 A1* | 11/2005 | Wang et al. | 705/3 |
| 2005/0262190 A1 | 11/2005 | Mamou et al. | |
| 2006/0052945 A1 | 3/2006 | Rabinowitz et al. | |
| 2006/0168043 A1* | 7/2006 | Eisenberger et al. | 709/206 |
| 2006/0206523 A1* | 9/2006 | Gaurav et al. | 707/104.1 |

(Continued)

FOREIGN PATENT DOCUMENTS

| | | |
|---|---|---|
| TW | 200404220 | 3/2004 |
| TW | 238316 | 8/2005 |

OTHER PUBLICATIONS

Lyman et al., Applying the HL7 Reference Information Model to a Clinical Data Warehouse, 2003, pp. 4249-4255.*

(Continued)

*Primary Examiner* — Sherief Badawi
(74) *Attorney, Agent, or Firm* — Perkins Coie LLP

(57) ABSTRACT

A system for electronic transmission of electronic medical records includes an object model derived from a messaging protocol, the object model configured to generate metadata for electronic medical records provided through a user-specified form. The system also includes a database configured according to the object model, the database physically stores the metadata generated by the object model. A data bridge/ data set pair transforms the metadata from a first format utilized by the database to a second format utilized by a recipient institution and a messaging module transmits the electronic medical records in the second format to the recipient institution.

13 Claims, 4 Drawing Sheets

(56) References Cited

U.S. PATENT DOCUMENTS

2006/0277215 A1* 12/2006 Siegel .................. 707/104.1
2007/0016610 A1* 1/2007 Cohen et al. ............. 707/104.1
2008/0065452 A1* 3/2008 Naeymi-Rad et al. ........... 705/8

OTHER PUBLICATIONS

Sujansky, Heterogeneous Database Integration in Biomedicine, Elsevier Science, Jun. 8, 2001, pp. 285-298.
Takeda, Architecture for Networked Electronic Patient Record Systems, 2000. 161-167.
Taylor, Design of an Integrated Clinical Warehouse, 2004, pp. 1-9.
Co-Pending U.S. Appl. No. 11/431,900, filed May 9, 2006.
Notice of Examination Opinion from Taiwanese Intellectual Property Office, mailed Oct. 22, 2012, for Taiwan Patent Application No. 95124208, filed Jul. 3, 2006, with English Translation.
U.S. Appl. No. 60/679,429, filed May 9, 2005.
U.S. Appl. No. 60/718,951, filed Sep. 19, 2005.
International Search Report PCT/US2006/17933 dated Aug. 25, 2008, pp. 1-5.
Written Opinion PCT/US2006/17933 dated Aug. 25, 2008, pp. 1-5.
Lyman, Jason, et al. "Applying the HL7 Reference Information Model to a Clinical Data Warehouse", IEEE, copyright 2003, pp. 4249-4255.
Fernandez, E., et al. an analysis of modeling flaws in HL7 and JAHIS, ACM, copyright 03 2005, pp. 216-223.

* cited by examiner

HEALTH-CARE RELATED DATABASE MIDDLEWARE

RELATED APPLICATIONS

This application is a continuation-in-part of prior application Ser. No. 11/431,900, filed May 9, 2006, which claims priority to Provisional Application No. 60/679,429, filed May 9, 2005, and Provisional Application No. 60/718,951, filed Sep. 19, 2005.

FIELD OF THE INVENTION

At least one embodiment of the present invention pertains to electronic transmission of electronic medical records, and more specifically, to electronic transmission of medical records stored in a database according to a Health Level 7 (HL7) Reference Information Model (RIM).

BACKGROUND

Health Level 7 ("HL7") is a healthcare information technology ("IT") standards body that is responsible for establishing the messaging protocols for the electronic transmission of information among IT systems used in the healthcare industry. The HL7 communications protocols allow IT systems offered by different solutions providers (and even different systems offered by the same solutions provider) to communicate with each other in a standardized fashion. Laboratory Information Systems ("LIS"), Hospital Information Systems ("HIS"), Electronic Medical Records systems ("EMR") and specialized systems that facilitate Computerized Physician Order Entry ("CPOE") are among the types of systems used by healthcare providers that typically support HL7 messaging as a standard method for communication. When information originated by one system must be shared with others, those systems are likely to require a specialized interface to do so. This is almost always true when the communication is between unrelated healthcare institutions, but it can also occur when systems within the same institution need to communicate.

The LIS, HIS and other healthcare IT systems produce information that is important to the diagnosis and treatment of patients. At times, this information is important to public health officials; most of the information that public health officials act upon in investigating incidents of communicable disease comes from reports of diagnostic test results confirming the incidence of infectious disease in a patient. As a result, electronic communication between LIS, HIS and other healthcare IT systems and the systems used by public health officials is important. For example, if a laboratory receives a diagnostic test result indicating that a patient may have a communicable disease, the laboratory is usually required by law to notify designated public health officials of the existence of the condition. Depending upon the circumstances, the physician who has ordered the test may also be required to report the positive test result to the public health department. While this type of reporting has traditionally been handled using manual processes such as telephonic reporting and/or mail or fax transmission of paper forms, the transmission of this information can be (and increasingly is being) handled in an automated fashion, using system-to-system communications often employing point-to-point interfaces. In situations where one or more steps in the notification process are handled electronically, the HL7 protocol has been the typical method of transmission. For reasons stated below, it is now the method mandated by the federal government.

As a result of a federal government initiative under the direction and control of the Centers for Disease Control and Prevention in Atlanta ("CDC"), a framework of coordinated standards and specifications, called the Public Health Information Network ("PHIN"), is now being advanced to facilitate the electronic transmission of information about communicable disease incidents from local public health departments to the CDC. PHIN will also perhaps facilitate the sharing of information among public health departments nationally. While the system was originally conceived as a disease surveillance network, in recent years its mandate has been expanded to include detection of incidents or outbreaks events that may indicate a bio-terrorist attack has occurred or is taking place. The CDC's vision for this network depends upon communication among healthcare providers, local, state and public health officials. The CDC might have mandated that all of these potential participants in the network use the same IT system to communicate. Instead, it chose to delegate responsibility for the deployment of IT systems to the participants themselves, leaving each free to adapt existing systems, build or buy new ones, so long as these systems were "interoperable" based upon criteria established by the CDC. One of the primary criteria for determining "interoperability" is the capability of each system to transmit messages using a standard format and structure. The CDC has adopted HL7 as the standard protocol for the format and structure of the data components of messages to be communicated across the Network.

While HL7 is widely used in the healthcare industry, it is not without its deficiencies. For example, the HL7 version 2 protocol is "flat". That is, it is not capable of sending nested information. Additionally, sometimes it is necessary to describe new events that are not part of the standard HL7 version 2 codes. As a result, new terms are implemented in free form or free text segments (so called "Z" segments). The problem with Z segments is that, by their nature, they hold information that (i) is unique to a particular institution and unlikely to be readily understood by other institutions, (ii) is of a type that cannot be accommodated in any other HL7 segment, and (iii) is in a format that is far more difficult to standardize. As a result, this dependence on the Z segment for the communication of important information undermines the utility of the HL7 "standard".

To overcome these deficiencies, HL7 conceived the version 3 Reference Information Model ("RIM"). The RIM is a static model of health and health care information as viewed within the scope of HL7 standards development activities. The formal representation of the RIM in messages employs the extensible markup language ("XML"). The RIM was designed in part to offer a more robust message structure that could accommodate the types of information traditionally communicated in Z segments. The CDC has specified that PHIN compliant systems should use both HL7 v2.x and HL7 v3.0 RIM messages.

In attempting to achieve interoperability for systems communicating across the Public Health Information Network, the CDC has had to deal with more than a standard messaging protocol. It has identified a wide variety of functions and specifications for "PHIN-compliant" systems. For example, the effort to ensure that all PHIN systems are capable of transmitting, receiving, storing and retrieving relevant information has led it to consider the optimal structure for the database within each system. By dictating the model that each system's database must follow, the CDC apparently has tried to ensure that PHIN-compliant systems will be able to handle the widest possible spectrum of data—including data about known diseases and typical incidents, as well as diseases that are as yet undiscovered, incidents never before observed, etc. The CDC has decided that the HL7 RIM—the model for the version 3.0 messaging structure, which is designed to allow for communication of a wide variety of "non-standard" information—should serve as the model for storage and retrieval of information communicated over the PHIN. That is, the CDC is requiring that data communicated using the HL7 RIM-based messaging standard should also be the schema for a database, the model for which is "derived from or directly mappable to the RIM". While this may seem logical to the layperson, structuring a database on a model behind a communications protocol is atypical, as the requirements that must be supported by a messaging standard are far different from those that would need to be addressed when designing an efficient, scalable database. Developing a RIM-based database that can perform up to the expectations of typical users of software solutions has proven challenging.

While PHIN-compliance is a major factor driving the need to overcome this challenge the RIM's usefulness goes beyond this regulatory impetus. A database modeled on the RIM would offer greater extensibility allowing RIM-based IT systems to better adapt to the ever-changing requirements of medical informatics necessitated by advances in medical science.

Existing healthcare IT systems (including those employed by public health officials) are likely to support communication using HL7 standards. In addition, many support HL7 v.2.x messages. However, these systems generally do not employ databases derived from or directly mappable to the RIM. The issue is further compounded in that each health institution will typically need to identify its existing data requirements, including (for example) the vocabularies it uses to label data elements, before communicating or writing that data to a database modeled on the RIM. As a result, unique implementations will be required to map each Network participant's data to a PHIN-compliant database.

In view of the foregoing, it may be useful to provide methods and systems that facilitate the mapping and storage of various disparate health-related data records to a RIM-compliant database.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

An embodiment by way of a non-limiting example includes a database translation architecture that has an object model for defining a variety of health-related classes and a plurality of data bridge/data set pairs wherein each data bridge is coupled to the object model. A plurality of external components are coupled to all but one of the data bridge/data set pairs of the plurality of data bridge/data set pairs wherein the plurality of external components are operative to send and receive data in formats unique to each external component such that each format is translated to and from the object model by each corresponding data bridge/data set pair. Also included is a database coupled to a remaining data bridge/data set pair not coupled to an external component wherein the database is responsive to data queries from the object model as translated by the remaining data bridge/data pair and the database and operative to deliver requested data back to the object model through the remaining data bridge/data set pair which is in turn sent to an external component that originally initiated the data query. Further, in additional embodiments, a concept descriptor is utilized. The concept descriptor uniquely identifies blocks of data for storage and retrieval. Moreover, the concept descriptor allows for well-defined, but new, datatypes to be consumed by the database.

In one embodiment, the object model is derived from a messaging protocol, the object model configured to generate metadata for electronic medical records provided through a user-specified form. The database is configured according to the object model, the database physically stores the metadata generated by the object model. A data bridge/data set pair transforms the metadata from a first format utilized by the database to a second format utilized by a recipient institution and a messaging module transmits the electronic medical records in the second format to the recipient institution.

In addition to the exemplary aspects and embodiments described above, further aspects and embodiments will become apparent by reference to the drawings and by study of the following descriptions.

BRIEF DESCRIPTION OF THE DRAWINGS

One or more embodiments of the present invention are illustrated by way of example and not limitation in the figures of the accompanying drawings, in which like references indicate similar elements.

DETAILED DESCRIPTION

References in this specification to "an embodiment", "one embodiment", or the like, mean that the particular feature, structure or characteristic being described is included in at least one embodiment of the present invention. Occurrences of such phrases in this specification do not necessarily all refer to the same embodiment.

Aspects of the present invention contemplates methods and systems of constructing a middleware that is capable of being mapped to any graphical user interface such that the collected data is properly received and stored in a RIM compliant manner. This is accomplished by utilizing a two-key primary key composed of an object identifier ("OID") of a RIM term and the actual term extension, a unified code table which is a relational meta-data structure that has a field that is common to all of the vocabularies in use and a document object model ("DOM") which defines various relationships between data types. Advantageously, aspects of the present invention allow for any type of graphical user interface to be conveniently mapped such that data collected by these user interfaces are stored in a RIM compliant manner as required by the CDC. These and other advantages will be detailed in subsequent sections.

Figure 1:
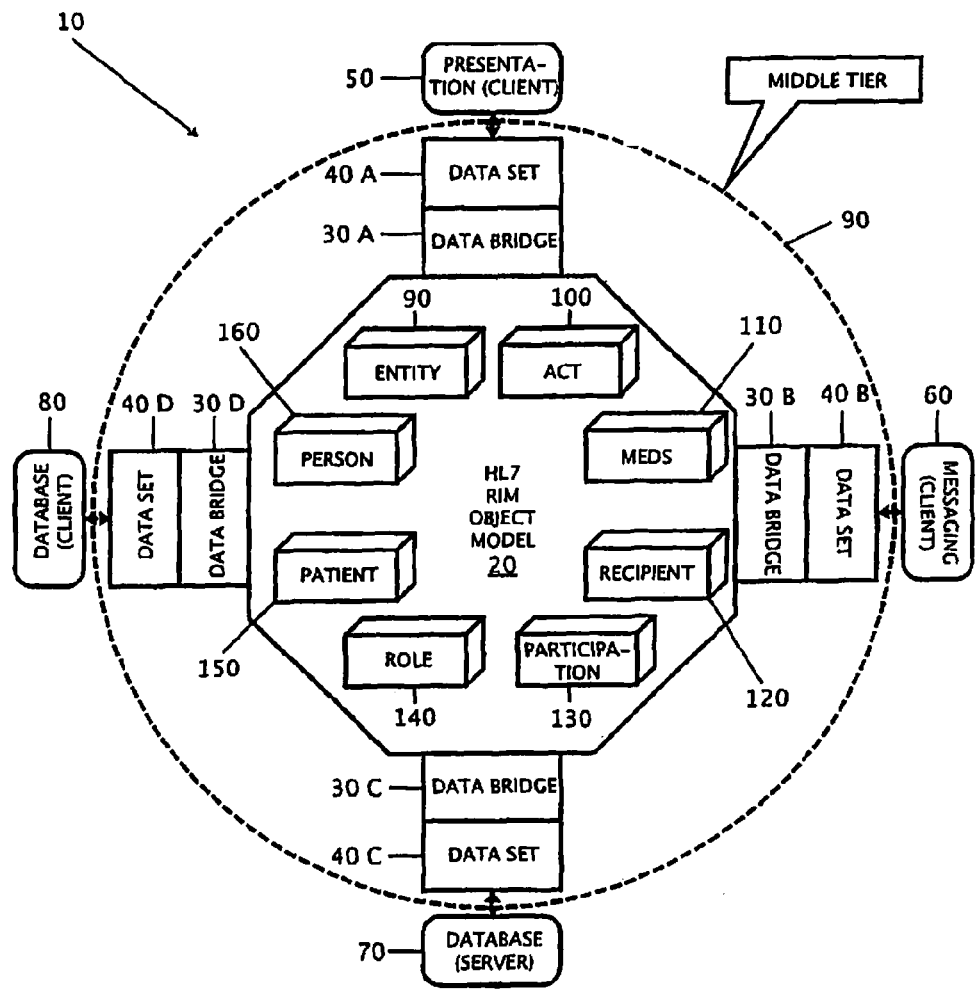
FIG. 1 illustrates a block diagram of a middleware architecture 10 capable of translating data into a RIM compliant data structure, in accordance with a particular implementation.

FIG. 1 illustrates a block diagram of a middleware architecture 10 capable of translating data into a RIM compliant data structure, in accordance with a particular implementation. Included in architecture 10 is a document object model 20, various data bridges (30A, 30B, 30C and 30D), associated data sets (40A, 40B, 40C and 40D) and various external interfaces such as a presentation client 50, a messaging client 60, a database server 70 and a database client 80 where data is stored in a RIM compliant manner. For convenience, the internal part of the architecture 10 will be referred to as a middle tier 90.

The middle tier 90 includes a common object-oriented schema that connects to sources and targets through the data bridges (30A, 30B, 30C and 30D) and target specific datasets (40A, 40B, 40C and 40D). The document object model 20 is the central organization of health data and application business logic. The object hierarchy can be derived from the CDC Public Health Logical Data Model 1.0, which itself is derived from the HL7 RIM. This provides for a common schema for which data can be transformed and translated into, connecting, for example a database 70 to a user interface such as presentation client 50.

The RIM document object model includes several classes that define the inter-relationships between various sets of data. These classes include entity 90, act 100, medications ("meds") 110, recipient 120, participation 130, role 140, patient 150 and person 160. To further illustrate what some of thee various classes mean, an entity 90 could be an institution such as a hospital, an act 100 could be prescribing a medication 110, a role 140 could be a doctor and so on.

The data bridges (30A, 30B, 30C and 30D) contains business logic to transfer data between the external interfaces (50, 60, 70 and 80) and the object model 20, using the datasets (40A, 40B, 40C and 40D) as an intermediary data cache. The data bridges (30A, 30B, 30C and 30D) determine which objects need to be instantiated and the attribute values to set. The data bridges (30A, 30B, 30C and 30D) also communicate directly with the datasets (40A, 40B, 40C and 40D) and the object model 20. Some the functions of the data bridges (30A, 30B, 30C and 30D) include object instantiation, object attribute setting, data type translation, computed field calculation, structured query language ("SQL") dialect calculation, query generation, dataset population, database updates and database trigger logic.

The datasets (40A, 40B, 40C and 40D) contain a representation of select data needed for transfer between client database 80 or server database 70. The datasets (40A, 40B, 40C and 40D) may contain numerous table and views of their relationships as is typically seen in a relational schema. It is intended to be in a format that makes it straight forward to update or derive data from the target data source. If the data source is the server database 70, then dataset 40C will represent data that is needed client database 80 or interfaces 50 and 60. Dataset 40D for interface 80 may be in a format that allows direct bindings from form controls to data fields datasets for a server and datasets for clients may be completely incompatible since the data is first transformed by the various data bridges (30A, 30B, 30C and 30D) into a common schema in the object model 20.

Figure 2:
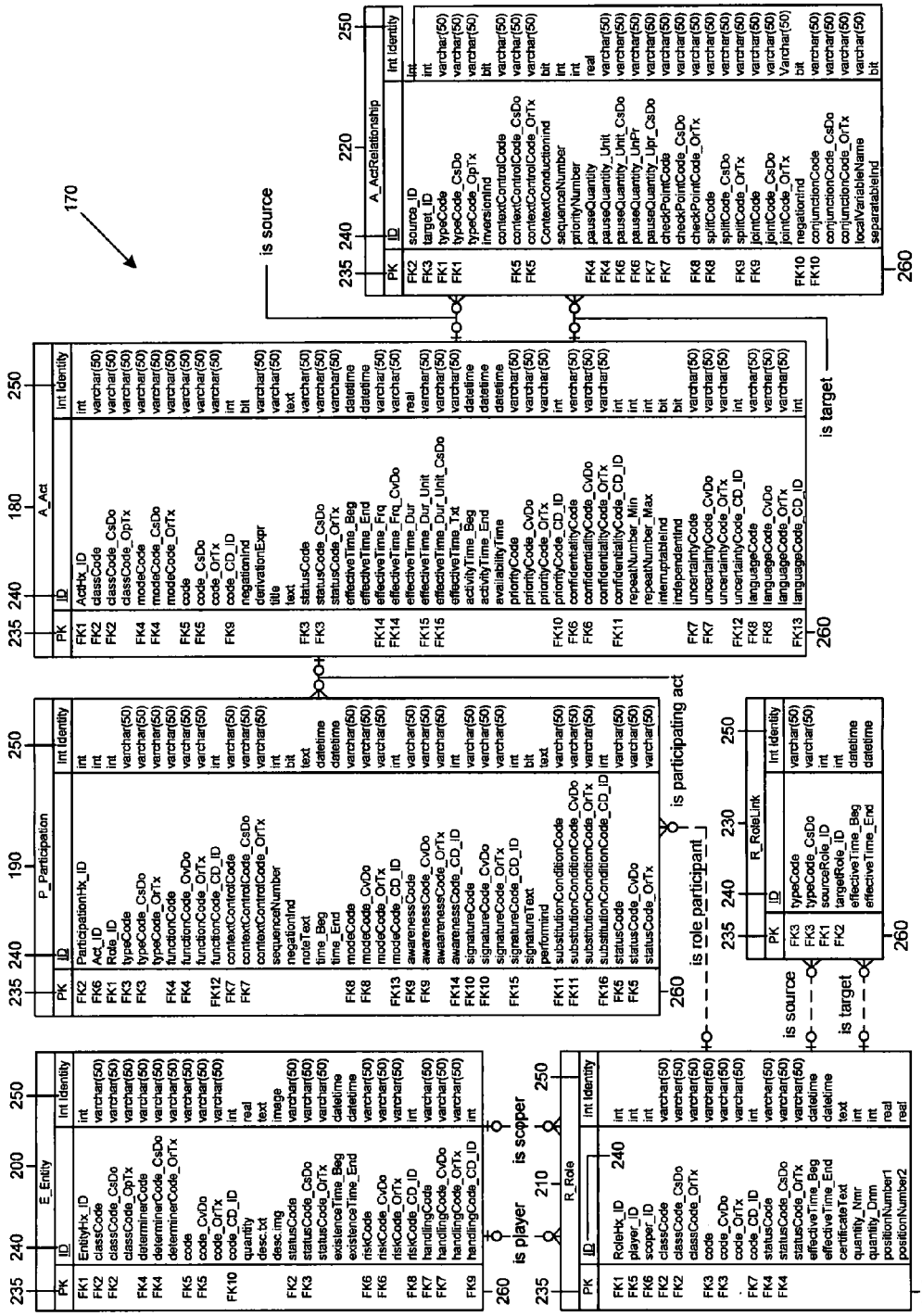
FIG. 2 illustrates a data model 170 used in the database server 70 of FIG. 1, in accordance with an exemplary embodiment.

FIG. 2 illustrates a data model 170 used in the database server 70 of FIG. 1, in accordance with an exemplary embodiment. Included in data model 170 are the major RIM classes act 180, participation 190, entity 200, role 210, act relationship 220 and role link 230. Act 180 represents actions that are executed and must be documented as health care is managed and provided. Participation 190 expresses the content for an act 180 in terms of such as who performed it, for whom it was done, etc. Entity 200 represents the physical things and beings that are of interest to and take part in health care. Role 210 establishes the roles that entities 200 play as they participate in health care acts 180. Act relationship 220 represents the binding of one act 180 to another, such as the relationship between an order for an observation and the observation event as it occurs. Role link 230 represents relationships between individual roles 210.

Included in each of the classes of data model 170 is the aforementioned two-key primary key 235 consisting of the OID 240 that a term comes from and the actual term extension 250. Also included are various foreign keys 260 for each individual OID and associated term extension. Foreign keys 260 point to locations in a unified code table (not shown). The unified code table is a relational meta-data structure that has a field that is common to all of the various, differing vocabularies that are employed by the health care industry. In an exemplary embodiment, data model 170 is defined using Microsoft's Visio® software which is capable of building a database and associated data definition files (".ddl").

Figure 3:
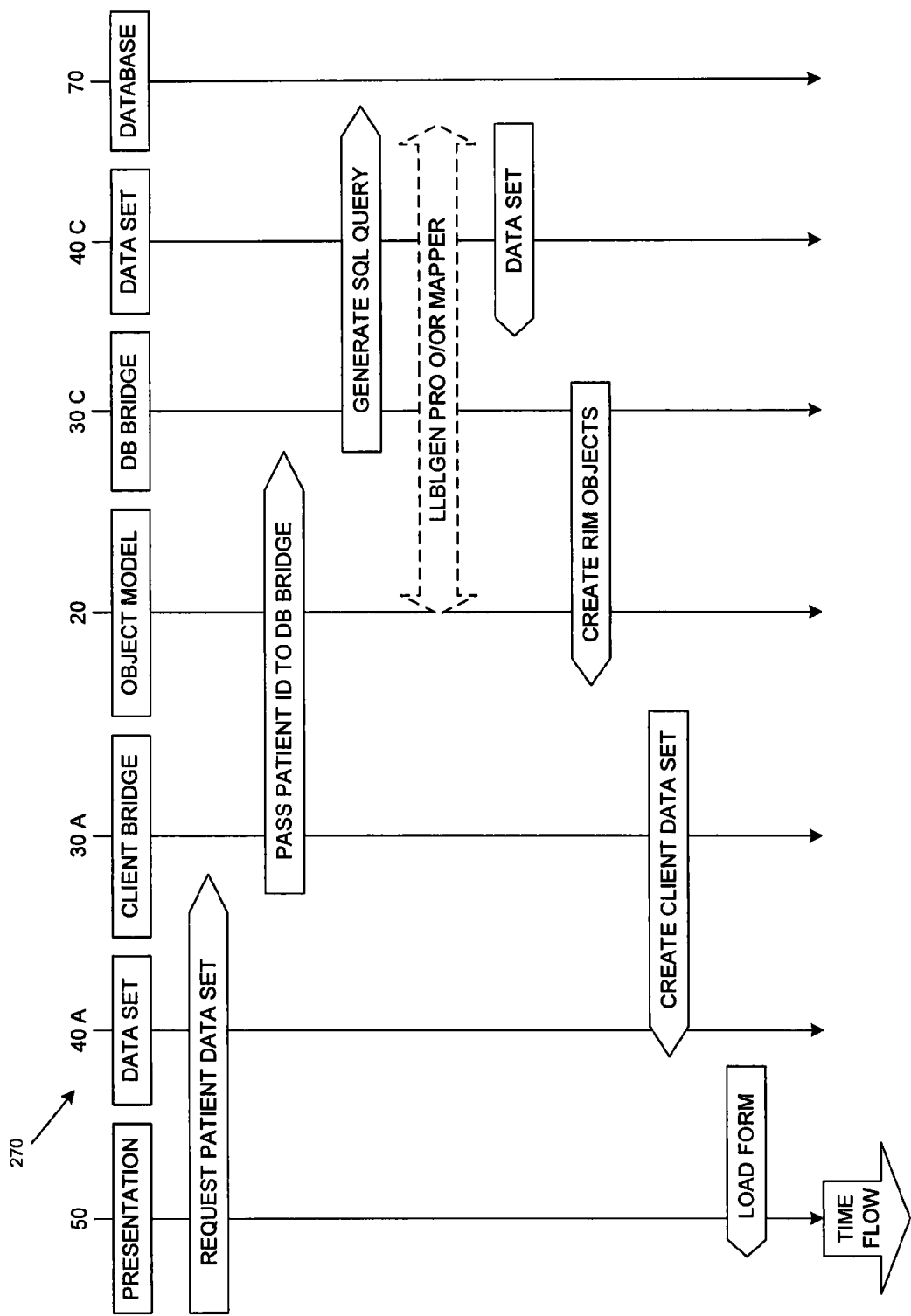
FIG. 3 is a class interaction diagram illustrating an exemplary data flow of the architecture 10 of FIG. 1, in accordance with an exemplary embodiment.

An exemplary data flow of architecture 10 of FIG. 1 will now be described. FIG. 3 is a class interaction diagram illustrating an exemplary data flow of the architecture 10 of FIG. 1, in accordance with an exemplary embodiment. Firstly, a patient dataset is requested from presentation client 50. The request is processed through the data set 40A and the data bridge 30A by passing a patient ID to the object model 20 and data bridge 30C. At the data bridge 30C, an SQL query is generated and sent to database 70 through data set 40C. In response, the requested dataset is sent from the database 70 to the object model 20 via data set 40C and data bridge 30C. During the transfer, RIM objects are created which are then used by the bridge 30A and data set 40A to create a client data set. In conclusion, a form containing the requested data is loaded at interface 50. In a preferred embodiment, an LLBL Gen Pro software tool is employed to automate the process shown in FIG. 3. LLBL Gen Pro is a data-access tier generator for .NET and it generates a complete data-access tier and business facade/support tier for use in an existing database schema set.

Figure 4:
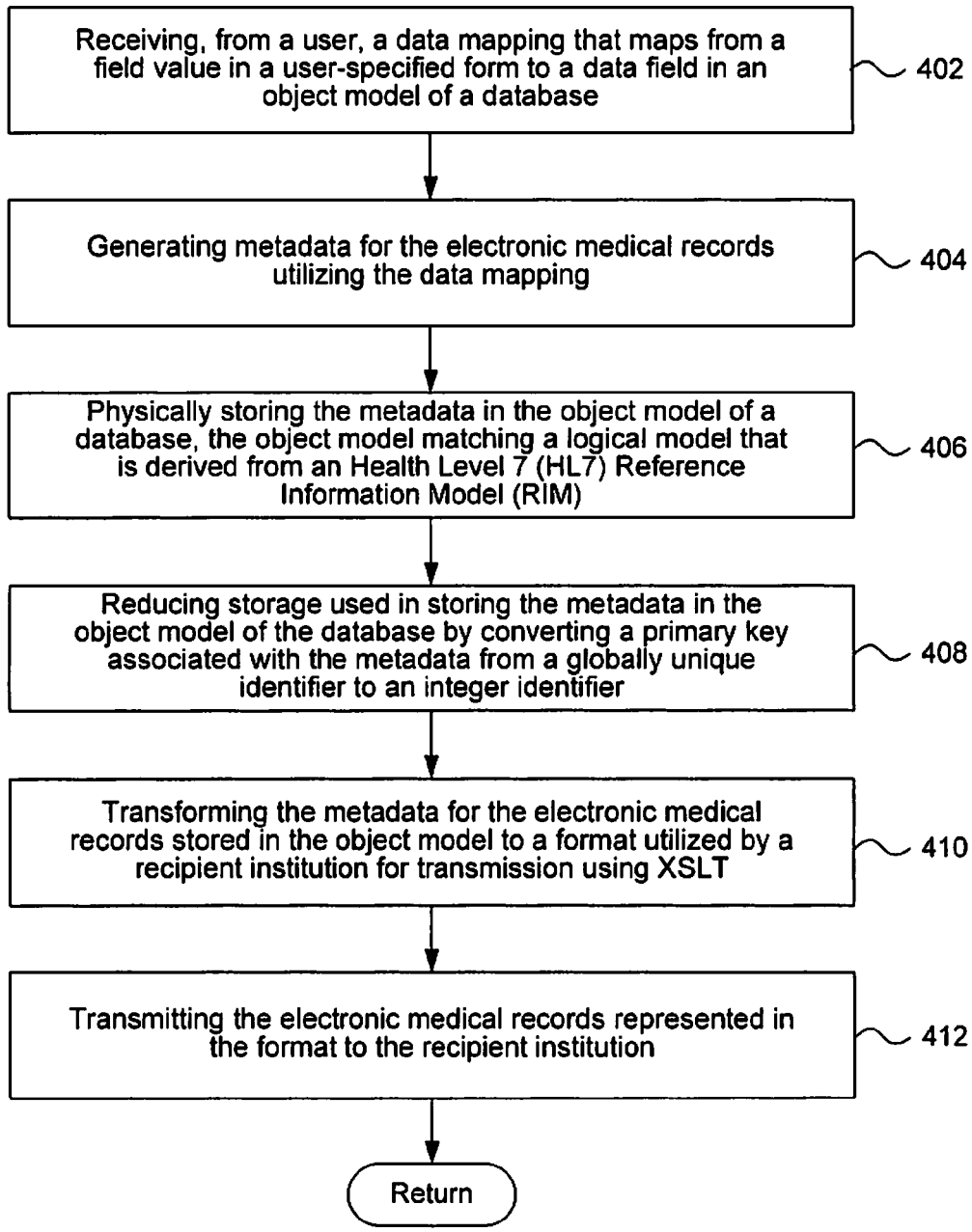
FIG. 4 is a flow diagram illustrating the electronic transmission of electronic medical records, in accordance with an exemplary embodiment.

FIG. 4 is a flow diagram illustrating the electronic transmission of electronic medical records, in accordance with an exemplary embodiment. At step 402, a form for receiving data to be stored as an electronic medical record is created by a user on, for example, presentation client 50. The form can be created using a drag and drop form creation wizard. In one embodiment, the drag and drop form creation wizard includes a mapping tool to that allows the user to map a field from the user created form to a data field of the RIM object model.

The mapping is used, at step 404, to generate metadata corresponding to the fields of the form that define the electronic medical records to be stored in the database and later to be transmitted to a third party. In one embodiment, the metadata is in an extensible markup language (XML) schema and the RIM object model is XML based. One such schema for the metadata can be WC3's XML Schema language, also know as XML Schema Definition (XSD). Other XML schema can be used for the metadata as should be apparent to one skilled in the art. The metadata generated by the form creation wizard is then, at step 406, physically stored in the RIM object model. In one embodiment, the metadata, i.e., the XSD document generated above, is stored as a field value in the RIM object model.

The user can then use the form to input medical records into the database. As described above, the object model is used to convert the data into a format that can be stored in a RIM compliant database. In one embodiment, as shown in step 408, instead of using a Globally Unique Identifier (GUID) associated with the medical record as a primary key, the GUID is converted to an integer and the integer is used as the primary key. This conversion reduces the amount of storage necessary to store the medical record in the database. The conversion also increases performance in accessing the medical record from the database. The electronic medical records stored in the database then be sent to a recipient institution using the HL7 V3 messaging protocol. The form can also be used for sending the electronic medical records to a recipient institution prior to the electronic medical records being stored in the database.

The Center for Disease Control (CDC) is an example of a recipient institution to which many messages are sent. The CDC requires messages to be sent in a particular format, e.g., a flat file, while the RIM object model, and the database based on the object model, stores medical records data in an XML format. When the user submits data to be sent to the CDC through a messaging client, the metadata stored in the RIM object model is transformed, at step 410, from the XML format to a format compatible with the CDC messaging protocol, e.g., a flat file in HL7. In one embodiment, Extensible Stylesheet Language Transformation (XSLT) is used for the transformation of the XML based electronic medical records to the format used by the recipient institution. The message can then be transmitted, at step 412, to the recipient institution in an acceptable format using the HL7 V3 messaging protocol.

The techniques introduced above can be implemented by programmable circuitry programmed or configured by software and/or firmware, or they can be implemented by entirely by special-purpose "hardwired" circuitry, or in a combination of such forms. Such special-purpose circuitry (if any) can be in the form of, for example, one or more application-specific integrated circuits (ASICs), programmable logic devices (PLDs), field-programmable gate arrays (FPGAs), etc.

Software or firmware for implementing the techniques introduced here may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing tool, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

The term "logic", as used herein, can include, for example, special-purpose hardwired circuitry, software and/or firmware in conjunction with programmable circuitry, or a combination thereof.

Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

The invention claimed is:

1. A method for electronic transmission of electronic medical records, the method comprising:
generating metadata for the electronic medical records provided by a user-specified form;
physically storing the metadata in an object model of a database, the object model paralleling a logical model that is derived from a Health Level 7 (HL7) messaging standard, wherein the object model is defined based on data mapping of fields to values in accordance with the HL7 messaging standard, wherein the object model utilizes a two-key primary key structure for each of a plurality of HL7 classes to store the metadata in compliance with the HL7 messaging standard, each two-key primary key structure including:
an object identifier key to identify a particular HL7 messaging term included in the HL7 messaging standard, the object identifier key being a first key of the two-key primary key structure;
a term extension key including a specific data from data blocks that are associated with the particular HL7 messaging term, the term extension key being a second key of the two-key primary key structure; and
wherein the object model further utilizes a foreign key in association with each two-key primary key structure for each class of the plurality of HL7 classes, and wherein the foreign key includes pointers to the metadata associated with the object model;
transforming the metadata for the electronic medical records stored in the object model to a format utilized by a recipient institution for transmission using the messaging protocol; and
transmitting the electronic medical records represented in the format to the recipient institution.

2. The method of claim 1, wherein, the data mapping of fields is specific to a medical institution.

3. The method of claim 1, wherein, the object model is XML-based.

4. The method of claim 1, wherein, XSLT is used to transform the metadata to the format.

5. The method of claim 1, further comprising, reducing storage used in storing the metadata in the object model of the database by converting a primary key associated with the metadata from a globally unique identifier to an integer identifier.

6. A system for transmitting electronic medical records, the system comprising:
a processor;
a memory coupled to the processor, the memory configured to store components of a transmitting system, the components including:
an object model paralleling a logical model that is derived from a Health Level 7 (HL7) messaging standard, wherein the object model is defined based on data mapping of fields to values in accordance with the HL7 messaging standard, wherein the object model utilizes a two-key primary key structure for each of a plurality of HL7 classes to store the metadata in compliance with the HL7 messaging standard, each two-key primary key structure including:
an object identifier key to identify a particular HL7 messaging term included in the HL7 messaging standard, the object identifier key being a first key of the two-key primary key structure;
a term extension key including a specific data from data blocks that are associated with the particular HL7 messaging term, the term extension key being a second key of the two-key primary key structure; and wherein the object model further utilizes a foreign key in association with each two-key primary key structure for each class of the plurality of HL7 classes, and wherein the foreign key includes pointers to the metadata associated with the object model;

a database configured according to the object model, the database configured to physically store the metadata generated by the object model, wherein the object model is configured to generate metadata for electronic medical records provided through a user-specified form;

a message generation module configured to transform the metadata from a first format utilized by the database to a second format utilized by a recipient institution; and a transmission module configured to transmit the electronic medical records in the second format to the recipient institution.

7. The system of claim 6, wherein, the data mapping of fields is specific to a medical institution.

8. The system of claim 6, wherein, the object model is XML-based.

9. The system of claim 6, wherein, XSLT is used to transform the metadata to the format.

10. The system of claim 6, wherein, the storage used in storing the metadata in the object model of the database is reduced by converting a primary key associated with the metadata from a globally unique identifier to an integer identifier.

11. A system for transmitting electronic medical records, the system comprising:

a processor;

a memory coupled to the processor, the memory configured to store components of a transmitting system, the components including:

a user interface configured to allow a user to specify a form for user input;

a data mapping tool configured to allow a user to map a field value from the specified form to a data field of an XML based object model paralleling a logical model that is derived from a Health Level 7 (HL7) Reference Information Model (RIM), the object model configured to generate metadata for electronic medical records input using the specified form, wherein the object model is defined based on data mapping of fields to values in accordance with the HL7 RIM, wherein the object model utilizes a two-key primary key structure for each of a plurality of HL7 classes to store the metadata in compliance with the HL7 RIM, each two-key primary key structure including:

an object identifier key to identify a particular HL7 messaging term included in the HL7 messaging standard, the object identifier key being a first key of the two-key primary key structure;

a term extension key including a specific data from data blocks that are associated with the particular HL7 messaging term, the term extension key being a second key of the two-key primary key structure; and wherein the object model further utilizes a foreign key in association with each two-key primary key structure for each class of the plurality of HL7 classes, and wherein the foreign key includes pointers to the metadata associated with the object model;

a database configured according to the object model, the database configured to physically store the metadata generated by the object model;

a message generation module configured to transform the metadata from a first format utilized by the database to a second format utilized by a recipient institution, wherein XSLT is used to transform the metadata to the second format; and a transmission module configured to transmit the electronic medical records in the second format to the recipient institution.

12. A method for electronic transmission of electronic medical records, the method comprising:

receiving, from a user, a data mapping that maps from a field value in a user-specified form to a data field in an object model of a database;

generating metadata for the electronic medical records utilizing the data mapping;

physically storing the metadata in the object model of a database, the object model paralleling a logical model that is derived from a Health Level 7 (HL7) Reference Information Model (RIM), wherein the object model is defined based on data mapping of fields to values in accordance with the HL7 RIM, wherein the object model utilizes a two-key primary key structure for each of a plurality of HL7 classes to store the metadata in compliance with the HL7 RIM, each two-key primary key structure including:

an object identifier key to identify a particular HL7 messaging term included in the HL7 messaging standard, the object identifier key being a first key of the two-key primary key structure;

a term extension key including a specific data from data blocks that are associated with the particular HL7 messaging term, the term extension key being a second key of the two-key primary key structure; and wherein the object model further utilizes a foreign key in association with each two-key primary key structure for each class of the plurality of HL7 classes, and wherein the foreign key includes pointers to the metadata associated with the object model;

transforming the metadata for the electronic medical records stored in the object model to a format utilized by a recipient institution for transmission using XSLT; and transmitting the electronic medical records represented in the format to the recipient institution.

13. A method for electronic transmission of electronic medical records, the method comprising:

generating metadata for the electronic medical records provided by a user-specified form;

physically storing the metadata in an object model of a database, the object model paralleling a logical model that is derived from a Health Level 7 (HL7) messaging standard, wherein the object model is defined based on data mapping of fields to values in accordance with the HL7 messaging standard, wherein the object model utilizes a two-key primary key structure for each of a plurality of HL7 classes to store the metadata in compliance with the HL7 messaging standard, each two-key primary key structure including:

an object identifier key to identify a particular HL7 messaging term included in the HL7 messaging standard, the object identifier key being a first key of the two-key primary key structure;

a term extension key including a specific data from data blocks that are associated with the particular HL7 messaging term, the term extension key being a second key of the two-key primary key structure; and wherein the object model further utilizes a foreign key in association with each two-key primary key structure for each class of the plurality of HL7 classes, and wherein the foreign key includes pointers to the metadata associated with the object model;

reducing storage used in storing the metadata in the object model of the database by converting a primary key associated with the metadata from a globally unique identifier to an integer identifier;

transforming the metadata for the electronic medical records stored in the object model to a format utilized by a recipient institution for transmission using the messaging protocol; and transmitting the electronic medical records represented in the format to the recipient institution.

\* \* \* \* \*